(12) United States Patent
Johnston et al.

(10) Patent No.: US 7,522,813 B1
(45) Date of Patent: Apr. 21, 2009

(54) REDUCING DISTORTION IN SCANNING FIBER DEVICES

(75) Inventors: Richard S. Johnston, Sammamish, WA (US); Charles David Melville, Issaquah, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/973,104

(22) Filed: Oct. 4, 2007

(51) Int. Cl.
G02B 6/00 (2006.01)

(52) U.S. Cl. .......................................... 385/147; 385/25

(58) Field of Classification Search ........................ None
See application file for complete search history.

(56) References Cited

U.S. PATENT DOCUMENTS

| | | | |
|---|---|---|---|
| 3,470,320 A | 9/1969 | Pike et al. | |
| 3,644,725 A | 2/1972 | Lochridge, Jr. | |
| 4,206,495 A | 6/1980 | McCaslin | |
| 4,234,788 A | 11/1980 | Palmer et al. | |
| 4,264,208 A | 4/1981 | Haberl et al. | |
| 4,710,619 A | 12/1987 | Haberl | |
| 4,743,283 A | 5/1988 | Borsuk | |
| 4,768,513 A | 9/1988 | Suzuki | |
| 4,770,185 A | 9/1988 | Silverstein et al. | |
| 4,782,228 A | 11/1988 | Westell | |
| 4,821,117 A | 4/1989 | Sekiguchi et al. | |
| 4,831,370 A * | 5/1989 | Smoot ........................... | 345/31 |
| 4,872,458 A | 10/1989 | Kanehira et al. | |
| 4,948,219 A | 8/1990 | Seino et al. | |
| 4,963,018 A | 10/1990 | West | |
| 5,081,350 A | 1/1992 | Iwasaki et al. | |
| 5,172,685 A | 12/1992 | Nudelman | |
| 5,178,130 A | 1/1993 | Kaiya | |
| 5,185,835 A | 2/1993 | Vial et al. | |
| 5,315,383 A | 5/1994 | Yabe et al. | |
| 5,360,968 A | 11/1994 | Scott | |
| 5,454,807 A * | 10/1995 | Lennox et al. ................. | 606/15 |
| 5,455,669 A | 10/1995 | Wetteborn | |
| 5,459,570 A | 10/1995 | Swanson et al. | |

(Continued)

FOREIGN PATENT DOCUMENTS

EP 1077360 2/2001

(Continued)

OTHER PUBLICATIONS

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

(Continued)

*Primary Examiner*—Uyen Chau N Le
*Assistant Examiner*—Mike Stahl
(74) *Attorney, Agent, or Firm*—Blakely Sokoloff Taylor & Zafman, LLP (57) ABSTRACT

Methods of reducing distortion in scanning fiber devices are disclosed. In one aspect, a method includes changing an intensity of light transmitted through a cantilevered optical fiber of a scanning fiber device. The method also includes changing a setpoint temperature for the scanning fiber device based at least in part on the change in the intensity of the light. Other methods, apparatus, systems, and machine-readable mediums are also disclosed.

32 Claims, 8 Drawing Sheets

U.S. PATENT DOCUMENTS

| | | | |
|---|---|---|---|
| 5,557,444 A | 9/1996 | Melville et al. | |
| 5,596,339 A | 1/1997 | Furness, III et al. | |
| 5,627,922 A | 5/1997 | Koelman et al. | |
| 5,664,043 A | 9/1997 | Donaldson et al. | |
| 5,694,237 A | 12/1997 | Melville | |
| 5,695,491 A | 12/1997 | Silverstein | |
| 5,701,132 A | 12/1997 | Kollin et al. | |
| 5,751,465 A | 5/1998 | Melville et al. | |
| 5,784,098 A | 7/1998 | Shoji et al. | |
| 5,822,073 A | 10/1998 | Yee et al. | |
| 5,822,486 A | 10/1998 | Svetkoff et al. | |
| 5,894,122 A | 4/1999 | Tomita | |
| 5,903,397 A | 5/1999 | Melville et al. | |
| 5,913,591 A | 6/1999 | Melville | |
| 5,939,709 A | 8/1999 | Ghislain et al. | |
| 5,969,871 A | 10/1999 | Tidwell et al. | |
| 5,982,528 A | 11/1999 | Melville | |
| 5,982,555 A | 11/1999 | Melville et al. | |
| 5,991,048 A | 11/1999 | Karlson et al. | |
| 5,995,264 A | 11/1999 | Melville | |
| 6,046,720 A | 4/2000 | Melville et al. | |
| 6,049,407 A | 4/2000 | Melville | |
| 6,061,163 A | 5/2000 | Melville | |
| 6,069,698 A | 5/2000 | Ozawa et al. | |
| 6,069,725 A | 5/2000 | Melville | |
| 6,097,353 A | 8/2000 | Melville et al. | |
| 6,154,321 A | 11/2000 | Melville et al. | |
| 6,157,352 A | 12/2000 | Kollin et al. | |
| 6,166,841 A | 12/2000 | Melville | |
| 6,191,761 B1 | 2/2001 | Melville et al. | |
| 6,204,832 B1 | 3/2001 | Melville et al. | |
| 6,220,711 B1 | 4/2001 | Melville et al. | |
| 6,243,186 B1 | 6/2001 | Melville et al. | |
| 6,257,727 B1 | 7/2001 | Melville | |
| 6,263,234 B1 | 7/2001 | Engelhardt et al. | |
| 6,281,862 B1 | 8/2001 | Tidwell et al. | |
| 6,285,505 B1 | 9/2001 | Melville et al. | |
| 6,288,816 B1 | 9/2001 | Melville et al. | |
| 6,291,819 B1 | 9/2001 | Hartley | |
| 6,294,775 B1 | 9/2001 | Seibel et al. | |
| 6,317,548 B1 * | 11/2001 | Rockwell et al. | 385/123 |
| 6,369,953 B2 | 4/2002 | Melville et al. | |
| 6,388,641 B2 | 5/2002 | Tidwell et al. | |
| 6,411,838 B1 | 6/2002 | Nordstrom et al. | |
| 6,441,359 B1 | 8/2002 | Cozier et al. | |
| 6,492,962 B2 | 12/2002 | Melville et al. | |
| 6,535,183 B2 | 3/2003 | Melville et al. | |
| 6,538,625 B2 | 3/2003 | Tidwell et al. | |
| 6,560,028 B2 | 5/2003 | Melville et al. | |
| 6,563,105 B2 | 5/2003 | Seibel et al. | |
| 6,627,903 B1 | 9/2003 | Hirayanagi | |
| 6,700,552 B2 | 3/2004 | Kollin et al. | |
| 6,734,835 B2 | 5/2004 | Tidwell et al. | |
| 6,747,753 B1 | 6/2004 | Yamamoto | |
| 6,845,190 B1 | 1/2005 | Smithwick et al. | |
| 6,850,673 B2 | 2/2005 | Johnston, II et al. | |
| 6,856,712 B2 | 2/2005 | Fauver et al. | |
| 6,867,753 B2 | 3/2005 | Chinthammit et al. | |
| 6,959,130 B2 | 10/2005 | Fauver et al. | |
| 6,975,898 B2 | 12/2005 | Seibel | |
| 6,977,631 B2 | 12/2005 | Melville et al. | |
| 7,068,878 B2 | 6/2006 | Crossman-Bosworth et al. | |
| 7,123,790 B2 | 10/2006 | Rosman et al. | |
| 7,159,782 B2 | 1/2007 | Johnston et al. | |
| 7,184,150 B2 | 2/2007 | Quadling et al. | |
| 7,189,961 B2 | 3/2007 | Johnston et al. | |
| 7,230,583 B2 | 6/2007 | Tidwell et al. | |
| 7,252,236 B2 | 8/2007 | Johnston et al. | |
| 2001/0051761 A1 | 12/2001 | Khadem | |
| 2001/0055462 A1 | 12/2001 | Seibel | |
| 2002/0062061 A1 | 5/2002 | Kaneko et al. | |
| 2002/0064341 A1 | 5/2002 | Fauver et al. | |
| 2002/0093467 A1 | 7/2002 | Tidwell et al. | |
| 2002/0093563 A1 | 7/2002 | Cline et al. | |
| 2002/0097498 A1 | 7/2002 | Melville et al. | |
| 2002/0139920 A1 | 10/2002 | Seibel et al. | |
| 2003/0010825 A1 | 1/2003 | Schmidt et al. | |
| 2003/0010826 A1 | 1/2003 | Dvorkis et al. | |
| 2003/0016187 A1 | 1/2003 | Melville et al. | |
| 2003/0142042 A1 | 7/2003 | Tidwell et al. | |
| 2003/0202361 A1 | 10/2003 | Johnston et al. | |
| 2004/0061072 A1 | 4/2004 | Gu et al. | |
| 2004/0122328 A1 | 6/2004 | Wang et al. | |
| 2004/0153030 A1 | 8/2004 | Novak et al. | |
| 2004/0196213 A1 | 10/2004 | Tidwell et al. | |
| 2004/0212851 A1 | 10/2004 | Osakabe | |
| 2004/0254474 A1 | 12/2004 | Seibel et al. | |
| 2005/0020926 A1 | 1/2005 | Wiklof et al. | |
| 2005/0025368 A1 | 2/2005 | Glukhosvsky | |
| 2005/0085708 A1 | 4/2005 | Fauver et al. | |
| 2005/0085721 A1 | 4/2005 | Fauver et al. | |
| 2005/0182295 A1 | 8/2005 | Soper et al. | |
| 2005/0238277 A1 | 10/2005 | Wang et al. | |
| 2006/0072843 A1 | 4/2006 | Johnston | |
| 2006/0072874 A1 | 4/2006 | Johnston | |
| 2006/0077121 A1 | 4/2006 | Melville et al. | |
| 2006/0138238 A1 | 6/2006 | Johnston et al. | |
| 2006/0149134 A1 | 7/2006 | Soper et al. | |
| 2006/0186325 A1 | 8/2006 | Johnston et al. | |
| 2006/0195014 A1 | 8/2006 | Seibel et al. | |
| 2006/0226231 A1 | 10/2006 | Johnston et al. | |
| 2006/0287647 A1 * | 12/2006 | Torchia et al. | 606/10 |
| 2007/0081168 A1 | 4/2007 | Johnston et al. | |
| 2007/0091426 A1 | 4/2007 | Johnston et al. | |
| 2007/0129601 A1 | 6/2007 | Johnston et al. | |
| 2007/0156021 A1 | 7/2007 | Morse et al. | |
| 2007/0273930 A1 | 11/2007 | Berier et al. | |

FOREIGN PATENT DOCUMENTS

| | | |
|---|---|---|
| EP | 1864606 | 12/2006 |
| GB | 2057709 | 4/1981 |
| GB | 2378259 | 2/2003 |
| WO | WO-9300551 | 1/1993 |
| WO | WO-0174266 | 10/2001 |
| WO | WO-03019661 | 3/2003 |
| WO | WO-2004/040267 | 5/2004 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041459 | 4/2006 |
| WO | WO-WO2006041452 | 4/2006 |
| WO | WO-2006071216 | 7/2006 |
| WO | WO-WO 2006071216 | 7/2006 |
| WO | WO-2006096155 | 9/2006 |
| WO | WO-2006/106853 | 10/2006 |
| WO | WO-2007070831 | 6/2007 |
| WOWO-WO 2008/033168 | | 3/2008 |

OTHER PUBLICATIONS

Brown, Christopher, et al., "A Novel Design for a Scanning Fiberoptic Endoscope", *Human Interface Technology Laboratory, University of Washington, Seattle, WA 98195*, Presented at SPIE's Regional Meeting of Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition, BED-vol.51*. (Nov. 11-16, 2001), 165-166.

Chen, Tailian, et al., "Experiment of Coalescence of Dual Bubbles on Micro Heaters", *Department of Mechanical Engineering, University of Florida, Gainesville, FL 32611-6300, USA.*, Printed from the Internet Aug. 13, 2006, 1-10.

Fauver, Mark, et al., "Microfabrication of fiber optic scanners", (*2002*) *In Proceedings of Optical Scanning II, SPIE 4773, pp. 102-110.*, 9 pages.

Seibel, Eric J., et al., "A full-color scanning fiber endoscope", *Optical Fibers and Sensors for Medical Diagnosis and Treatment Applications. Ed. I Gannot. Proc. SPIE vol. 6083*, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE vol. 4957*, (2003), 46-55.

Seibel, Eric J., et al., "Modeling optical fiber dynamics for increased efficiencies in scanning fiber applications", *Optical Fibers and Sensors for Medical Applications V, proceedings of SPIE vol. 5691*, (2005), 42-53.

Seibel, Eric J., et al., "P-37: Optical fiber scanning as a microdisplay source for a wearable low vision aid", *Society for Information Display SID 2002, Boston, MA*, (May 19-24, 2002), 1-4.

Seibel, Eric J., et al., "Prototype scanning fiber endoscope", *Optical Fibers and Sensors for Medical Applications II, Proc. of SPIE, vol. 4616*, (2002), 1-7.

Seibel, Eric J., et al., "Single fiber flexible endoscope: general design for small size, high reosolution, and wide field of view", *Human Interface Technology Laboratory, College of Engineering, University of Washington, Seattle, WA*, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), P-178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", *2000 Annual Fall Meeting Abstracts T4.57*, (2000), 1.

Smithwick, Quinn Y., et al., "54.3: Modeling and Control of the Resonant Fiber Scanner for Laser Scanning Display of Acquisition", *Department of Aeronautics and Astronautics, University of Washington, Seattle, WA SID 03 Digest*, (2003), 1455-1457.

Smithwick, Quinn Y., et al., "A Nonlinear State-Space Model of a Resonating Single Fiber Scanner for Tracking Control: Theory and Experiment", *Transactions of the ASME, vol. 126*, (Mar. 2004), 88-101.

Smithwick, Quinn Y., et al., "Control Aspects of the Single Fiber Scanning Endoscope", (*2001*) *SPIE Optical Fibers and Sensors for Medical Applications, 4253, 176-188.*, 15 pages.

Smithwick, Quinn Y., et al., "Depth Enhancement using a Scanning Fiber Optical Endoscope", *Department of Aeronautics, Human Interface Technology Laboratory, University of Washington, Seattle, Washington*, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE vol. 6083.*, (2006), 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE vol. 4876 (2003)*, (2003), 72-83.

Wang, Wei-Chih, et al., "Micromachined optical waveguide cantilever as a resonant optical scanner", *Department of Mechanical Engineering, University of Washington, Seattle, WA 98195, Sensors and Actuators A 102.* (2002), 165-175.

"PCT/US2007/009598 International Search Report", (Jan. 3, 2008), 3 pages.

Brown, Christopher M., et al., "Optomechanical design and fabrication of resonant microscanners for a scanning fiber endoscope", *Optical Engineering, vol. 45, XP002469237*, (Apr. 2006), pp. 1-10.

Smithwick, Y. J., et al., "An error space controller for a resonating fiber scanner: simulation and implementation", *Journal of Dynamic Systems, Measurement and Control, Fairfiled, N.J., U.S.*, vol. 128, No. 4, XP009095153, ISSN: 0022-0434, (Dec. 2006), pp. 899-913.

PCT Search Report and Written Opinion, PCT/US2007/021604, (Jun. 2, 2008), 1-13 pgs.

\* cited by examiner

REDUCING DISTORTION IN SCANNING FIBER DEVICES

BACKGROUND

1. Field

Embodiments of the invention pertain to scanning fiber devices. In particular, embodiments of the invention pertain to reducing image distortion in scanning fiber devices by changing setpoint temperatures for the scanning fiber devices based at least in part on changes in intensity of light transmitted through the scanning fiber devices.

2. Background Information

Scanning fiber devices are well known in the arts. The scanning fiber device may include a single, cantilevered optical fiber that may be vibrated and scanned in one or two dimensions in a scan pattern to acquire an image of a target area.

In acquiring an image of the target area, the scanning fiber device may scan an illumination spot through an optional lens system and over the target area in the scan pattern. Backscattered light may be captured, for example by a photosensor, in time series.

In acquiring the image, it is generally desirable to accurately know the position of the optical fiber for each and every point of the scan. Positional inaccuracy may tend to result in distortion of the image acquired.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1:
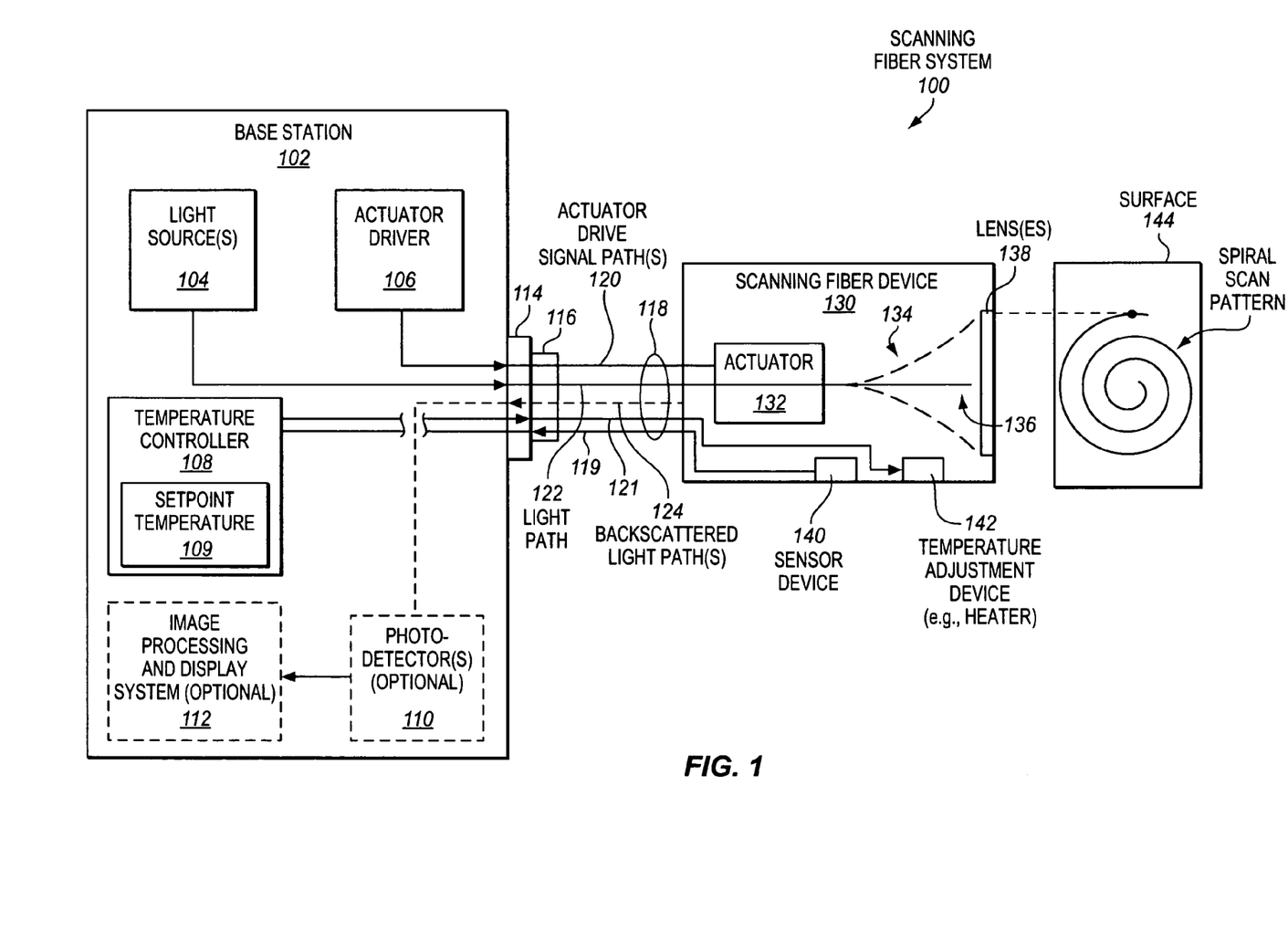
FIG. 1 is a block diagram of an example scanning fiber system, according to embodiments of the invention.

FIG. 1 is a block diagram of an example scanning fiber system 100, according to embodiments of the invention. In various embodiments of the invention, the scanning fiber system may take the form of a scanning fiber endoscope, scanning fiber boroscope, scanning fiber microscope, other type of scanning fiber scope, scanning fiber bar code reader, or other scanning fiber image acquisition device known in the art.

As is known, endoscopes represent instruments or devices to be inserted into a patient to acquire images inside a body cavity, lumen, or otherwise look inside the patient. Examples of suitable types of endoscopes include, but are not limited to, bronchoscopes, colonoscopes, gastroscopes, duodenoscopes, sigmoidoscopes, ureteroscopes, sinuscopes, boroscopes, and thorascopes, to name just a few examples.

The scanning fiber system has a two-part form factor that includes a base station 102 and a scanning fiber device 130, although such a two-part form factor is not required. The scanning fiber device is electrically and optically coupled with the base station through one or more cables 118. In particular, the scanning fiber device includes a connector 116 to connect, mate, or otherwise couple with a corresponding connector interface 114 of the base station. Electrical and optical signals may be exchanged between the base station and the scanning fiber device through the connector interface. The scope of the invention is not limited to any particular type of connector or connector interface.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

The base station includes one or more light sources 104. The one or more light sources may provide light to the scanning fiber device through the connector interface and a light path 122. Examples of suitable light sources include, but are not limited to, lasers, laser diodes, vertical cavity surface-emitting lasers (VCSELs), light-emitting diodes (LEDs), and combinations thereof. In various example embodiments of the invention, the one or more light sources may include a red light source, a blue light source, a green light source, a red-green-blue (RGB) light source, a white light source, an infrared light source, an ultraviolet light source, a high intensity therapeutic laser light source, or a combination thereof. Depending on the particular implementation, the one or more light sources may emit a continuous stream of light, modulated light, or a stream of light pulses. As will explained further below, in embodiments of the invention, different intensities of light may be provided from the one or more light sources to the scanning fiber device.

The base station also includes an actuator driver 106. The actuator driver may provide voltages or other electrical signals, referred to herein as actuator drive signals, to the scanning fiber device through the connector interface and one or more actuator drive signal paths 120. As one example, in one or more embodiments of the invention, the actuator driver may include one or more lookup tables or other data structures stored in a memory that may provide actuator drive signal values. The actuator drive signal values may potentially be adjusted based on calibration, such as, for example, as described in U.S. Patent Application 20060072843, entitled "REMAPPING METHODS TO REDUCE DISTORTIONS IN IMAGES", by Richard S. Johnston. As another example, the actuator driver may include a computer, processor, application specific integrated circuit (ASIC), or other circuit to generate the actuator drive signal values in real time. The values may be digital and may be provided to a digital-to-analog converter of the actuator driver. One or more amplifiers of the actuator driver may amplify the analog versions of the actuator drive signals. These are just a few illustrative examples of suitable actuator drivers.

The scanning fiber device 130 includes a single cantilevered free end portion of an optical fiber 134 and an actuator 132. The actuator may receive the actuator drive signals from the base station. The actuator may vibrate, move, or otherwise actuate the cantilevered optical fiber based on, and responsive to, the received actuator drive signals. In embodiments of the invention, the actuator drive signals may be operable to cause the actuator to move the cantilevered optical fiber in a two-dimensional scan pattern. Examples of suitable two-dimensional scan patterns include, but are not limited to, spiral scan patterns, propeller scan patterns, Lissajous scan patterns, circular scan patterns, oval scan patterns, raster scan patterns, and the like.

The cantilevered optical fiber may receive the light from the one or more light sources. The light may be emitted from a distal end or tip 136 of the cantilevered optical fiber, while the optical fiber is scanned. The emitted light may be passed through one or more lenses 138 to generate a focused beam or illumination spot, which may be moved across a surface 144 in the scan. In the illustration, a spiral scan pattern is shown and a dot shows a position of the illumination spot at a particular point in time.

The scanning fiber system may be used to acquire an image of a surface. In acquiring the image of the surface, the scanning fiber device may scan an illumination spot through the lens system and over the surface in the scan. Backscattered light from the surface may be captured at different points in time during the scan and used to construct the image.

Different ways of capturing or collecting the backscattered light are possible. One or more optical fibers, or other backscattered light paths 124, may optionally be included to collect and convey backscattered light back to one or more optional photodetectors 110 of the base station. Alternatively, the scanning fiber device may optionally include photodetectors proximate a distal tip thereof. As shown, the base station may include an optional image processing and display system 112 to generate images based on light detected by the photodetectors. A display may be included in the base station or may be externally connected to the base station.

In constructing the image, it is generally desirable to accurately know the position of the cantilevered optical fiber and/or illumination beam for each and every point of the scan. Positional inaccuracy may tend to result in distortion of the image constructed. Knowing the actuator drive signal that is used to scan the cantilevered optical fiber may allow the position of the illumination spot to be estimated for each pixel point during the scan pattern.

In practice however, environmental variables, manufacturing variables, the sensitivity of the scanning fiber device around the resonant frequency, and/or other factors, may tend to limit the accuracy of such estimates. If desired, calibration and remapping as described in U.S. Pat. App. Pub. No. 20060138238 by Johnston et al. may be performed to help reduce image distortion due to certain of such factors. However, this calibration and remapping approach generally does not yield completely undistorted images for all the possible variations of environmental variables.

Temperature is one environmental variable that may affect the operation of a scanning fiber device. Temperature variation, if unaccounted for, may tend to add to the positional inaccuracy of the cantilevered optical fiber and/or illumination beam. Without limitation, this may be, due at least in part, to the affect of temperature variation on the properties of the cantilevered optical fiber and/or the affect of temperature variation on the properties of materials associated with the movement of the cantilevered optical fiber. Such positional inaccuracy may tend to add distortion to the image acquired using the scanning beam device and is generally undesirable. Accordingly, in embodiments of the invention, temperatures within a scanning fiber device may be adjusted. U.S. patent application Ser. No. 11/521,523, filed on Sep. 13, 2006, by Johnston et al., discloses temperature adjustment in scanning beam devices.

Referring again to FIG. 1, the scanning beam device includes an optional sensor device 140. The sensor device is enclosed within a housing of the scanning fiber device. The sensor device may sense or measure a condition within the housing. Commonly the sensor device may include a temperature sensor, such as, for example, a thermocouple, resistive temperature device (RTD), or thermistor.

The sensor device is electrically coupled with a temperature controller 108 of the base station. The temperature controller 108 has a setpoint temperature 109 for the scanning fiber device. The sensor device may provide the sensed condition to the temperature controller. The temperature controller may use the sensed condition and the setpoint temperature to control a temperature within the scanning fiber device. The temperature controller is electrically coupled with, or otherwise in communication with, a temperature adjustment device 142 of the scanning fiber device. The temperature controller may provide one or more temperature control signals to the temperature adjustment device through the interface.

Commonly, the temperature adjustment device may include a heater, such as, for example, an electrical resistance heater. Examples of suitable electrical resistance heaters include, but are not limited to, coil resistance heaters, thin film resistance heaters, cartridge resistance heaters, positive temperature coefficient (PCT) resistance heaters, other resistance heaters known in the arts, and combinations thereof. Alternatively, the temperature adjustment device may include a cooler. Examples of suitable coolers include, but are not limited to, Peltier devices, other thermoelectric cooling devices known in the arts, and heat pipes.

The temperature adjustment device may adjust temperatures within the housing or otherwise adjust temperatures of the cantilevered optical fiber based on the temperature control signals. Often, this adjustment of the temperature may be used to regulate or maintain a substantially constant temperature within the housing to reduce positional inaccuracy and/or image distortion, although the scope of the invention is not limited in this respect.

A simplified base station has been shown and described in order to avoid obscuring the description. Other representative components that may potentially be included in the base station include, but are not limited to, a power source, a user interface, a memory, and the like. Furthermore, the base station may potentially include supporting components like clocks, waveform generators, amplifiers, digital-to-analog converters, analog-to-digital converters, and the like.

Figure 2:
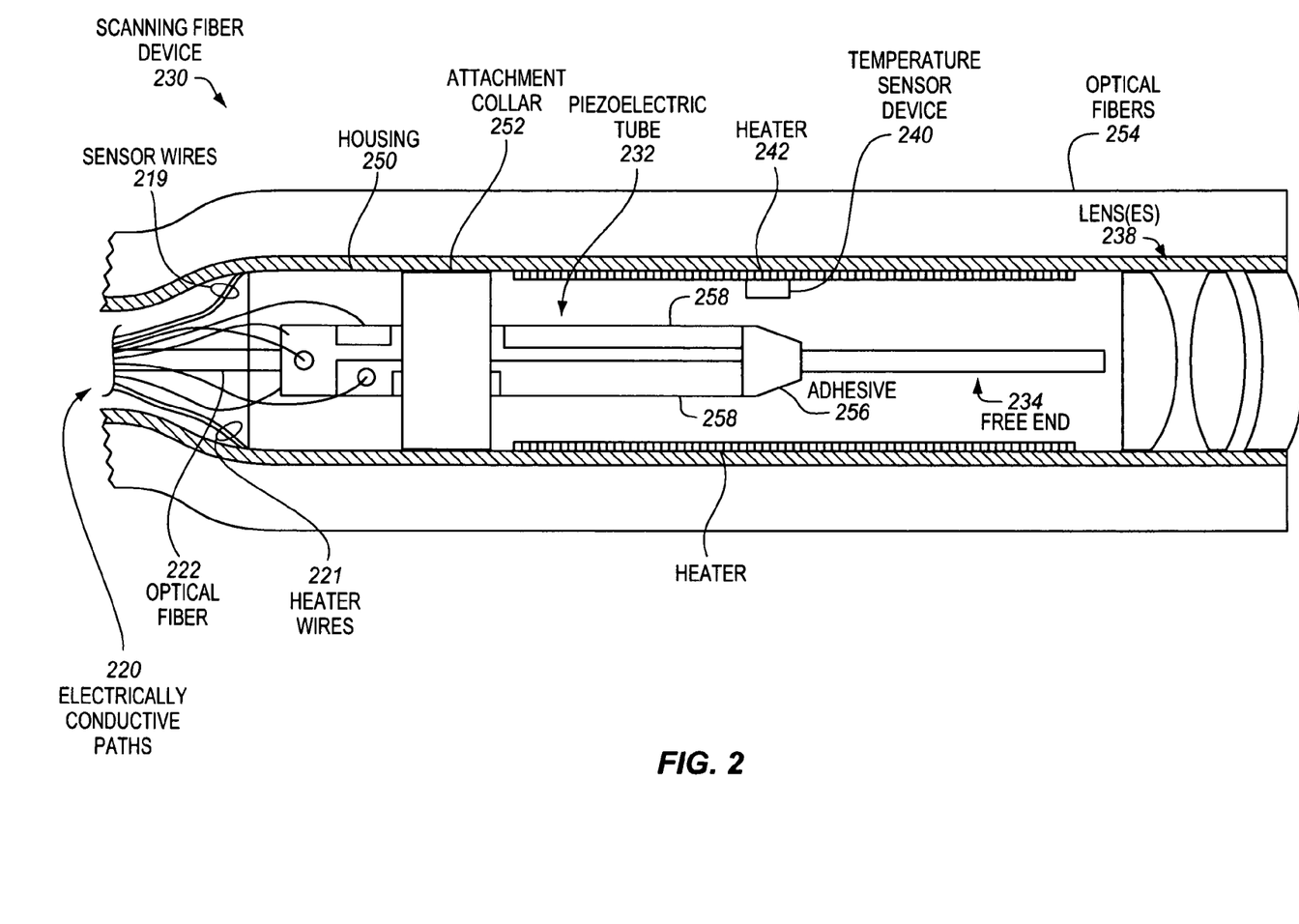
FIG. 2 is a cross-sectional side view of a particular example of a scanning fiber device, according to embodiments of the invention.

FIG. 2 is a cross-sectional side view of a particular example of a scanning fiber device 230, according to embodiments of the invention. This particular scanning fiber device is well suited for use as an endoscope or other relatively small device. In other implementations the design and operation may vary considerably. Accordingly, it is to be appreciated that this particular scanning fiber device is merely illustrative.

The scanning fiber device includes a housing 250. In one or more embodiments, the housing may be relatively small and hermetically sealed. For example, the housing may be generally tubular, have a diameter that is about 5 millimeters (mm) or less, and have a length that is about 20 mm or less. In some embodiments, the diameter may be about 1.5 mm or less, and the length may be about 12 mm or less. The housing often includes one or more lenses 238. Examples of suitable lenses include those manufactured by Pentax Corporation, although other lenses may optionally be used.

A piezoelectric tube 232, representing one possible type of actuator, is included in the housing. In one or more embodiments of the invention, the piezoelectric tube may include a PZT 5A material, although this is not required. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass. An attachment collar 252 may be used to attach the piezoelectric tube to the housing. The piezoelectric tube may be inserted through a tightly fitting generally cylindrical opening of the attachment collar. Other configurations for the piezoelectric tube and housing are also possible.

A portion of an optical fiber 222 is inserted through a generally cylindrical opening in the piezoelectric tube. A cantilevered free end portion 234 of the optical fiber extends beyond an end of the piezoelectric tube within the housing. An adhesive 256 may be used to restrain, adhere, or otherwise couple the optical fiber to the piezoelectric tube. Examples of suitable adhesives include, but are not limited to: Copper-Bond brand epoxy resin, which is commercially available from Super Glue Corporation, of Rancho Cucamonga, Calif.; TRA-BOND F123 brand adhesive, which is commercially available from TRA-CON, Inc., of Bedford, Mass.; 5 Minute® Epoxy brand epoxy resin, which is commercially available from Devcon, of Glenview, Ill.; and SuperGlue brand cyanoacrylate, which is commercially available from Super Glue Corporation. The mechanical properties of these materials may tend to vary differently with temperature. Other configurations of the piezoelectric tube and cantilevered optical fiber are also possible. The cantilevered optical fiber is flexible and may be actuated by the piezoelectric tube.

The scanning fiber device includes a temperature sensor device 240 to sense a temperature within the housing. One particular example of a suitable thermistor includes a multi-layer NTC Panasonic series ERTJ size 0201 (about 2 mm×1 mm) thermistor, which is commercially available from Panasonic, of Secaucus, N.J. This thermistor has a resistance of about 10 kΩ. In one or more embodiments of the invention, the thermistor may optionally be grinded down by approximately half in order to further reduce its size, although this is not required. If done, the resistance may change and the thermistor should be recalibrated.

The scanning beam device includes a heater 242 to increase the temperature within the housing. The heater may include a coil resistance heater. The coil resistance heater may be formed by winding a small diameter wire into a coil. The wire may optionally be folded or doubled back on itself and wound into a bifilar coil. This may allow both ends of the wire to be on the same side. Additional windings per unit length may optionally be provided at the ends to promote even temperatures across the length of the heater. An example of suitable wire is 36 μm EVANOHM® nickel-chromium resistance wire, available from Wilbur B. Driver Co., which has a resistance of about 400 Ω/ft, although the scope of the invention is not limited to this particular type of wire. As shown, the coil resistance heater may be placed on an inside of the inner wall of the housing. As shown, the coil may surround the free end portion of the optical fiber and may span a substantial length thereof. In one particular embodiment of the invention, the heater includes a bifilar coil of 36 μm EVANOHM® nickel-chromium resistance wire that is folded or doubled back on itself, having about 300 loops, a length of about 6 mm, and a diameter of about 0.9 mm, however this particular heater is not required. Such a heater may be capable of producing around 30 milliwatts of heat on average.

As shown, in one or more embodiments of the invention, the temperature sensor device may be positioned proximate the adhesive. Temperature may affect the properties of the adhesive (e.g., make it more rigid or flexible), and thereby affect the movement of the free end portion of the optical fiber. Placing the thermistor or other temperature sensor device proximate the adhesive may promote accurate measurement of the temperature of the adhesive. By way of example, for such a small device to be inserted into a patient, the thermistor is generally within about 2 mm of the adhesive, and in some embodiments the thermistor may be within about 0.5 mm of the adhesive, although the scope of the invention is not so limited. As further shown, in one or more embodiments, the thermistor may be adhered to the inside surface of the coils of the heater.

A number of electrically conductive paths 220 are run from the base station (not shown) to a proximal end of the scanning fiber device. The electrically conductive paths may carry electrical signals to the piezoelectric tube, the temperature sensor device, and the heater. By way of example, each of four electrically conductive paths may be soldered to or otherwise electrically coupled with respective ones of four, quadrant electrodes on the piezoelectric tube. These four paths may carry drive signals to the piezoelectric tube to cause it to scan the optical fiber. One conductive path may optionally be provided to a ground electrode inside the piezoelectric tube, although this is not required. Two sensor wires 219 may be electrically coupled with the temperature sensor. Two heater wires 221 may be electrically coupled with the heater. The sensor wires and heater wires may optionally be run along an inner surface of the housing. One or more notches may be provided in the attachment collar at the interface abutting the inner surface of the housing to accommodate passage of these wires.

As shown, one or more optical fibers 254 may optionally be included around the outside of the housing to collect and convey backscattered light from an illumination spot back to one or more photodetectors, for example located in a base station. Alternatively, one or more photodetectors may be included at or near a distal tip of the scanning fiber device, or omitted entirely.

Figure 3:
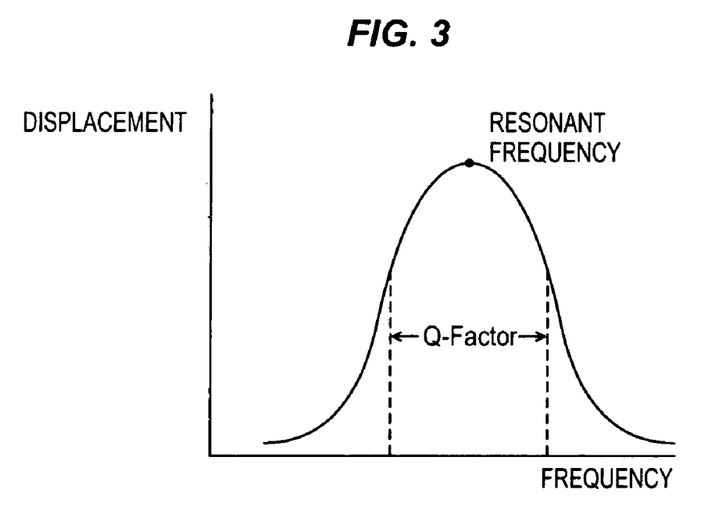
FIG. 3 is a graph of example resonant gain characteristics of a cantilevered optical fiber operated in a first mode of resonance.

FIG. 3 is a graph of example resonant gain characteristics of a cantilevered optical fiber operated in a first mode of resonance. Frequency of vibration of the cantilevered optical fiber is plotted on the horizontal axis versus displacement of the cantilevered optical fiber on the vertical axis.

The displacement increases around, and peaks at, a mechanical or vibratory resonant frequency. This is due to an increase in the resonant gain of the cantilevered optical fiber. In the illustration, the displacement has a relatively Gaussian dependency on frequency, with the greatest displacement occurring at the resonant frequency. In practice, there may be significant deviation from such a Gaussian dependency, although the displacement still typically peaks at the resonant frequency.

While the optical fiber may be vibrated at various frequencies, in embodiments of the invention, the optical fiber may be vibrated at or around, for example within a Q-factor of, its resonant frequency, or harmonics of the resonant frequency. As is known, the Q-factor is the ratio of the height of the resonant gain curve to the width of the curve. Due to the increased resonant gain, vibrating the optical fiber at or around the resonant frequency may help to reduce the amount of energy, or magnitude of the actuator drive signal, needed to achieve a given displacement to perform a given scan.

Scanning at or around the resonant frequency, however, may put the position of the optical fiber about 90° out of phase relative to the actuator drive signal. This phase shift is relatively sensitive to frequency proximate the resonant frequency. Changes in temperature of the cantilevered optical fiber may cause corresponding changes in the resonant frequency. These changes in the resonant frequency may cause phase shift distortions in images acquired with the scanning fiber device. These distortions may take the form of rotation of the entire image. Other distortions may also result from changes in the temperature of the cantilevered optical fiber. The resonant frequency may also change with the amplitude of the actuator drive signal, and the amount may be different at different temperatures.

Changes in temperature of an adhesive used to adhere the cantilevered optical fiber to the actuator tube may also cause distortion. Higher temperatures may tend to make the adhesive more flexible, whereas lower temperatures may tend to make the adhesive more rigid. Such changes in the rigidity of the adhesive may change the way the cantilevered optical fiber moves for a given actuation. Furthermore, in one or more embodiments of the invention, a drive signal may be applied to the actuator tube to remove energy from the cantilevered optical fiber to stop, or at least slow, the movement of the cantilevered optical fiber after a frame of image acquisition, such as, for example, as described in U.S. Pat. No. 7,159,782, entitled "METHOD OF DRIVING A SCANNING BEAM DEVICE TO ACHIEVE HIGH FRAME RATES", by Richard S. Johnston et al. Increased flexibility of the adhesive at higher temperatures may tend to make removal of the energy of the cantilevered optical fiber different. As one additional factor, changes in the temperature of the adhesive may tend to expand or contract the adhesive. This may potentially change the length of the cantilevered optical fiber, which may correspondingly affect the resonant frequency.

In embodiments of the invention, the intensity of light transmitted through a cantilevered optical fiber of a scanning fiber device may change. There are various potential reasons for the intensity to change. Some scanning fiber systems may include an Automated Gain Control (AGC) unit or circuit that may change the intensity of the light, for example, to try to maintain a constant intensity of backscattered light collected. Some scanning fiber systems may allow a user or system to select a particular intensity, for example from multiple different intensities, or a continuous spectrum of different intensities. By way of example, this capability may allow the user the flexibility to choose an intensity that is appropriate for a given ambient brightness or otherwise appropriate for a particular implementation. Some scanning fiber systems may allow either full-color (e.g., RGB) images or monochromatic images (e.g., black-and-white images, blue-only images, etc.) to be constructed. The intensity used for the full-color images may be greater than the intensity used for the monochromatic images. Some scanning fiber systems, such as endoscopes, may have the ability to switch between different modes of operation. For example, an endoscope may be capable of switching between a full-color image acquisition mode and an infrared, ultraviolet, or fluorescent light mode. The intensities of these modes may be different. As another example, an endoscope may be capable of switching between an image acquisition mode and a high-powered therapeutic light mode, such as, for example, suitable to perform laser ablation. The intensity of the high-powered therapeutic light mode is generally significantly greater than that of the image acquisition mode. These are just a few illustrative examples.

One associated challenge is that the intensity of light transmitted through the cantilevered optical fiber has been observed to affect distortion in images acquired with the scanning fiber device. It is presently believed that the intensity may affect the temperature of the cantilevered optical fiber and/or one or more materials associated with the movement of the cantilevered optical fiber. Without wishing to be bound by theory, it is presently further believed that some of the light transmitted through the cantilevered optical fiber may be reflected from the distal tip of the cantilevered optical fiber. At least some of this reflected light may enter the cladding of the cantilevered optical fiber and may heat the cladding. Deviation of the cleavage angle of the distal tip of the cantilevered optical fiber from about 90° may tend to increase the amount of reflected light that enters the cladding. Still without wishing to be bound by theory, in the particular case of the cantilevered optical fiber being adhered to the piezoelectric tube with an adhesive, at least some of the reflected light in the cladding may enter the adhesive and may heat the adhesive. Such heating may tend to increase the temperature of the adhesive and/or the cantilevered optical fiber. Generally, the greater the intensity of the light the greater the increase in temperature.

This increase in temperature may occur even if the temperature control system attempts to control the temperature sensor at a constant setpoint temperature. The temperature sensor may sense a temperature reflecting some of the extra heat from the adhesive and/or the cantilevered optical fiber due to the increased intensity of light. This sensed temperature may be communicated to the temperature controller. The temperature controller may correspondingly control a slight reduction in the amount of heat output from the heater in an attempt to maintain the temperature of the temperature sensor at the constant setpoint temperature. However, the temperature sensor is typically at least a small distance away from the cantilevered optical fiber and/or the adhesive. Even such a small distance of separation may result in even a slight temperature gradient between the temperature sensor and the cantilevered optical fiber and/or the adhesive. As a result, even if the temperature control system attempts to maintain the temperature sensor at the constant setpoint temperature, the temperature of the cantilevered optical fiber and/or adhesive may tend to increase slightly due to the heating resulting from the increased intensity of light.

Such increases in temperature may tend to make the cantilevered optical fiber and/or the adhesive more flexible or otherwise change their mechanical properties. This may correspondingly tend to change the way in which the cantilevered optical fiber is actuated or moved for the given actuator drive signals. This may lead to positional inaccuracy that may tend to result in distortion of the image acquired. Accordingly, changes in intensity, if unaccounted for, may potentially contribute to distortion in the images acquired.

If desired, calibration and remapping similar to that described in U.S. Pat. App. Pub. No. 20060138238 by Johnston et al. may be performed to help reduce such image distortion due to changes in intensity. However, this calibration and remapping approach is not a perfect solution when there are a large number of possible intensity values, since collecting data for the large number of intensity values may take a relatively large amount of time and/or a relatively large amount of memory would be used to store the associated calibration data.

Figure 4:
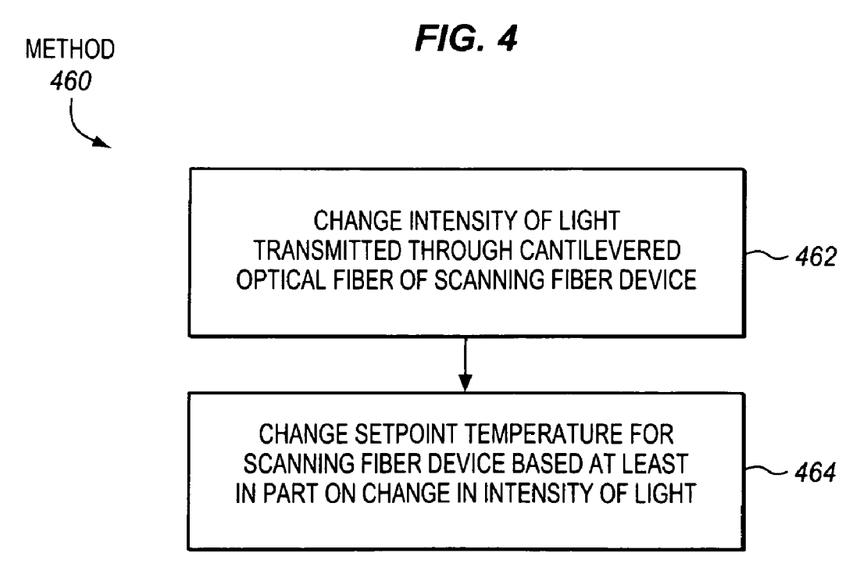
FIG. 4 is a block flow diagram of a method of reducing distortion in images acquired with a scanning fiber device by changing a setpoint temperature for the scanning fiber device based at least in part on a change in intensity of light transmitted through a cantilevered optical fiber of the scanning fiber device, according to embodiments of the invention.

FIG. 4 is a block flow diagram of a method 460 of reducing distortion in images acquired with a scanning fiber device, according to embodiments of the invention. The method includes changing an intensity of light transmitted through a cantilevered optical fiber of the scanning fiber device, at block 462. The intensity may change for any of the reasons previously discussed, or for other reasons entirely.

The method also includes changing a setpoint temperature for the scanning fiber device based, at least in part, on the change in the intensity of the light, at block 464. The setpoint temperature may be the target temperature that a temperature controller, such as, for example, located in a base station, may attempt to control or achieve in the scanning fiber device. In various embodiments, the setpoint temperature may be changed either before, concurrently with, or after the change in the intensity.

In embodiments of the invention, the change in the setpoint temperature may be operable to maintain a temperature of the cantilevered optical fiber and/or the adhesive attached to the cantilevered optical fiber substantially constant irrespective of the change in the intensity. As used herein, the temperature is maintained "substantially constant" if the change is less than 50% of what the change would be if the setpoint temperature were not changed. In embodiments of the invention, the change in the setpoint temperature may be operable to substantially eliminate, or at least substantially reduce, distortion in an image acquired with the scanning fiber device that would otherwise occur due at least in part to the change in the intensity. As used herein, distortion is "substantially reduced" when it is reduced by at least 50% and distortion is "substantially eliminated" when it is reduced by at least 80%.

In order to reduce distortion, the change in the setpoint temperature may be in an opposite direction from the change in the intensity. For example, changing the intensity may include increasing the intensity, and changing the setpoint temperature may include decreasing the setpoint temperature. As another example, changing the intensity may include decreasing the intensity, and changing the setpoint temperature may include increasing the setpoint temperature. Changing the setpoint temperature in the opposite direction from the change in intensity may help to reduce distortion by offsetting or reducing a change in temperature of the cantilevered optical fiber and/or one or more materials associated with the movement of the cantilevered optical fiber (e.g. an adhesive if present), which would otherwise tend to occur due at least in part to the change in the intensity.

Without wishing to be bound by theory, an example may help to further illustrate certain concepts. Consider the scanning fiber device 230 of FIG. 2. Assume that an intensity of light transmitted through the cantilevered optical fiber 234 is increased. As previously discussed, this increase in intensity may tend to result in an increase in the temperature of the cantilevered optical fiber and/or the adhesive 256. This may tend to change the way the cantilevered optical fiber moves during acquisition of an image, which may tend to cause image distortion. However, in order to help offset the aforementioned increase in temperature, the setpoint temperature 109 at which a temperature controller of the base station attempts to control the temperature sensor device 240 may be decreased. As a result, the temperature controller may control a decrease in the amount of heat generated by the heater 242. This may result in a slight decrease in the temperature of the region around the cantilevered optical fiber that is heated by the heater. This decrease in temperature may create a slightly greater temperature differential between the region and the cantilevered optical fiber and/or the adhesive. This increased temperature differential may tend to increase the rate of heat transfer away from the cantilevered optical fiber and/or the adhesive, which are at a higher temperature than the region. This increased rate of heat transfer may help to cool or reduce the temperature of the cantilevered optical fiber and/or the adhesive. In short, the change in the setpoint temperature may help to reduce or offset a change in the temperature of the cantilevered optical fiber and/or the adhesive that would otherwise occur due at least in part to the change in the intensity.

Change in temperatures of the cantilevered optical fiber and/or the adhesive are generally expected to take place rapidly. However, in one or more embodiments of the invention, the setpoint temperature may optionally be changed incrementally or otherwise changed gradually within a period of not more than several seconds after the intensity is changed.

Embodiments of the invention may include determining the change in the setpoint temperature. In one or more embodiments, a user or system may manually determine the change in the setpoint temperature in real time during operation. By way of example, after a change in intensity, the user or system may incrementally change the setpoint temperature by relatively small amounts in an opposite direction from the change in intensity until the distortion is minimized or otherwise sufficiently reduced. However, such an approach may tend to be laborious and/or time consuming when intensities are changed frequently and/or when there are many possible intensity values.

As another option, in one or more embodiments, a user or system may use a predetermined relationship to determine the setpoint temperature or change in setpoint temperature. The predetermined relationship may relate various intensities of light transmitted through the cantilevered optical fiber to corresponding setpoint temperatures operable to reduce distortion in images. Examples of suitable predetermined relationships include, but are not limited to, calibration data, regression equations based at least in part on calibration data, theoretical equations (e.g., heat transfer equations), mathematical models (e.g., heat transfer models), mathematical and/or logical algorithms, and combinations thereof. The calibration data may include at least two pairs of data, each pair of data including a different intensity of light and a corresponding empirically determined different setpoint temperature.

Figure 5:
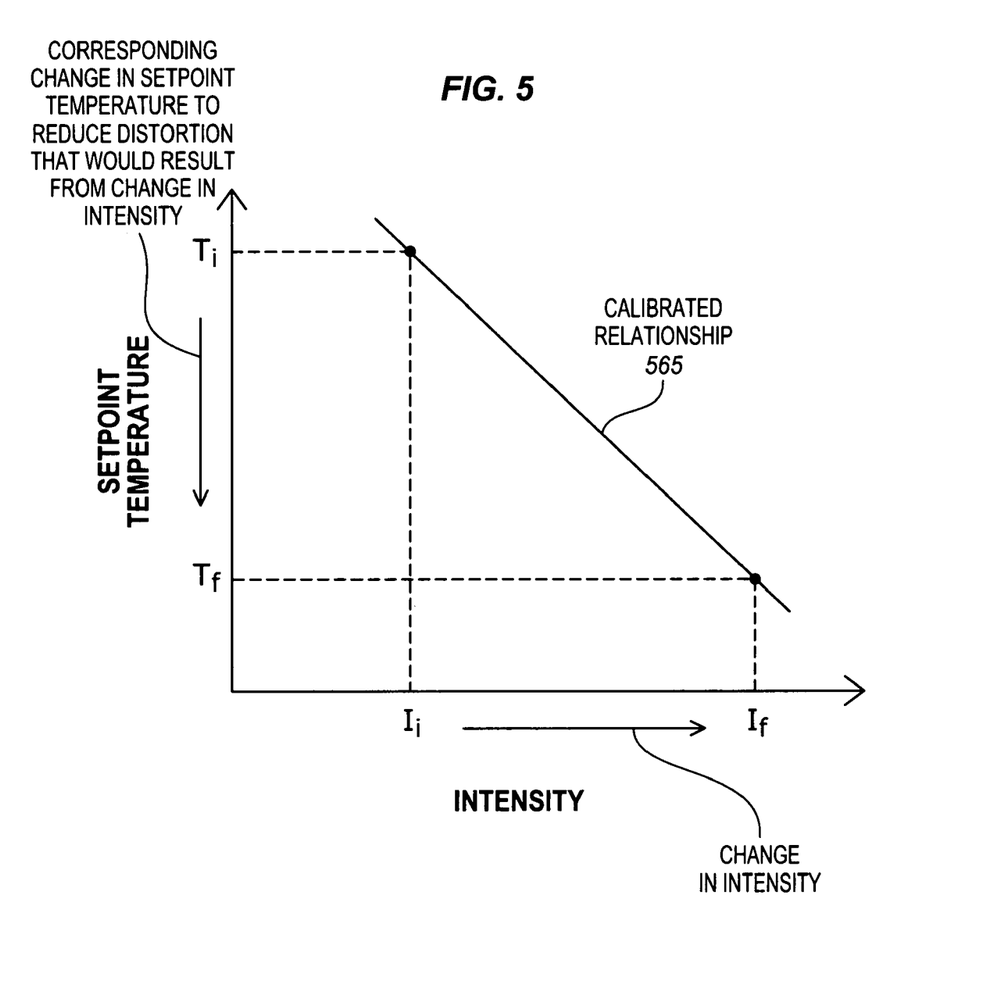
FIG. 5 is a graph showing that a predetermined relationship may be used to determine a change in a setpoint temperature, according to one or more embodiments of the invention.

FIG. 5 is a graph showing that a predetermined relationship may be used to determine a change in a setpoint temperature, according to one or more embodiments of the invention. The graph plots intensity of light on the horizontal axis, versus setpoint temperature on the vertical axis. A predetermined relationship 565 relates intensities of light transmitted through the cantilevered optical fiber to corresponding setpoint temperatures that are operable to substantially reduce distortion in images acquired with the scanning fiber device. The illustrated relationship is a straight line, for example a linear regression, although more sophisticated equations may optionally be used. Before a change, an initial intensity (Ii)

and initial temperature (Ti) are used. The intensity is then increased to a final intensity (If). To help reduce distortion that would otherwise result from the increase in intensity, the temperature is decreased to a final temperature (Tf).

Figure 6:
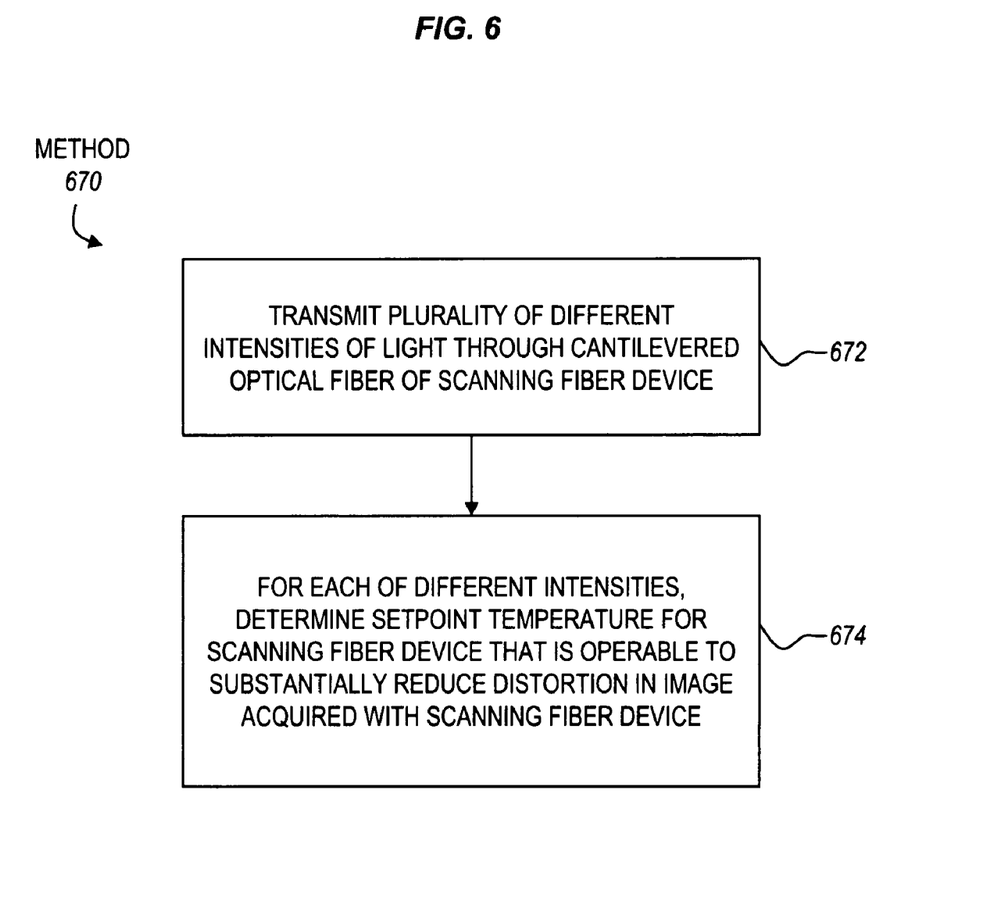
FIG. 6 is a block flow diagram of a method of calibrating a scanning fiber device, according to embodiments of the invention.

FIG. 6 is a block flow diagram of a method 670 of calibrating a scanning fiber device, according to embodiments of the invention. A plurality of different intensities of light may be transmitted through a cantilevered optical fiber of the scanning fiber device, at block 672. For each of the different intensities, a setpoint temperature for the scanning fiber device may be determined, at block 674. The setpoint temperature determined for each intensity may be operable to substantially reduce distortion in an image acquired with the scanning fiber device that would otherwise occur due at least in part to each intensity.

Figure 7:
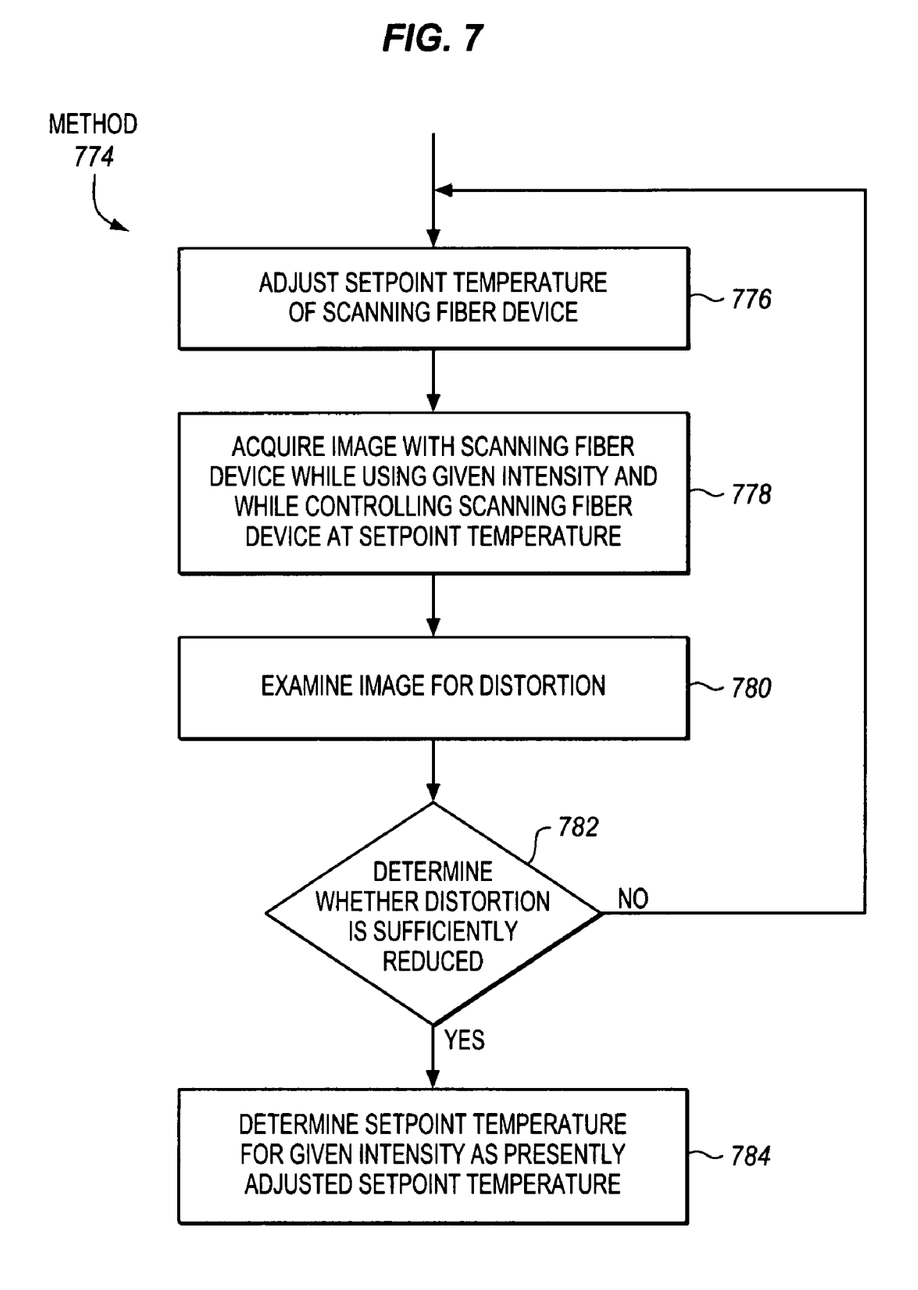
FIG. 7 is a block flow diagram of a detailed example of a method of determining a setpoint temperature for a given intensity of light, according to embodiments of the invention.

FIG. 7 is a block flow diagram of a detailed example of a method 774 of determining a setpoint temperature for a given intensity of light, according to embodiments of the invention. In one or more embodiments, the method may be used for each of the different intensities at block 674 in FIG. 6.

A setpoint temperature of a scanning fiber device may be adjusted, at block 776. As one example, the setpoint temperature may be changed by a relatively small or incremental amount in an opposite direction from a recent direction of change in intensity. Then, an image may be acquired with the scanning fiber device while using the given intensity and while controlling the scanning fiber device at the setpoint temperature, at block 778. Next, the acquired image may be examined for distortion, at block 780. The examination may either be manual or with the aid of image comparison software.

A determination may be made whether the distortion is sufficiently reduced by the adjustment of the temperature, at block 782. If the distortion is not sufficiently reduced (i.e., "no" is the determination), then the method may revisit block 776. Alternatively, if the distortion is sufficiently reduced (i.e., "yes" is the determination), then the setpoint temperature for the given intensity may be determined to be the presently adjusted setpoint temperature. The operations of adjusting the setpoint temperature, examining for distortion, and determining whether distortion is sufficiently reduced, may be performed manually by a user, automatically by a controller, or some of these operations may be performed manually by the user, while others may be performed automatically by the controller.

Figure 8:
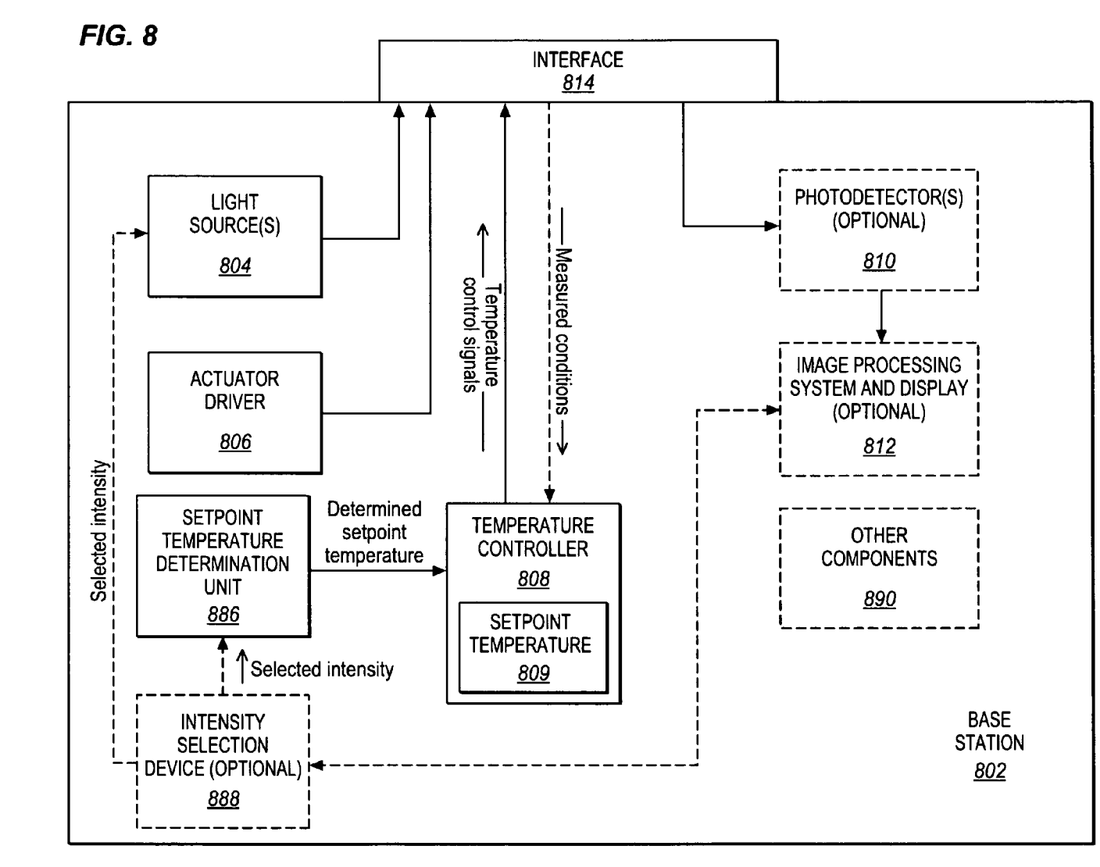
FIG. 8 is a block diagram of a base station for a scanning fiber image acquisition system, according to embodiments of the invention.

FIG. 8 is a block diagram of a base station 802 for a scanning fiber image acquisition system, according to embodiments of the invention. The base station 802 may optionally have some or all of the characteristics of the base station 102 of FIG. 1. To avoid obscuring the description, the discussion below will tend to focus primarily on the different or additional characteristics of the base station 802.

The base station has an interface 814 to connect or otherwise couple with a scanning fiber device. The base station has one or more light sources 804 optically coupled with the interface to provide light to the scanning fiber device through the interface. The base station has an actuator driver 806 electrically coupled with the interface to provide actuator drive signals to the scanning fiber device through the interface. The actuator drive signals may drive the movement or scanning of the cantilevered optical fiber.

The base station may optionally include one or more photodetectors 810 to detect backscattered light returned from the scanning fiber device to the base station. Alternatively, the photodetectors may be located outside of the base station. As shown, the base station may include an optional image processing and display system 812 to generate images based on detected light. A display may be included in the base station or may be externally connected to the base station. The base station may include other components 890 as previously discussed.

The base station may include an optional intensity selection device 888. The intensity selection device may select an intensity of light to be output by the one or more light sources 804. As shown, the intensity selection device may be electrically coupled with, or otherwise in communication with, the one or more light sources to provide the selected intensity.

One example of a suitable intensity selection device is an Automatic Gain Control (AGC) circuit or other unit. The amount of backscattered light detected by the scanning fiber device may tend to vary due to such factors as changing proximity of the distal tip of the scanning fiber device to a surface, or the like. The AGC unit may attempt to control the intensity of the backscattered light at a constant level. As shown, the AGC unit may receive an indication of the intensity of the backscattered light detected by the scanning fiber device, for example from the image processing and display system. The AGC unit may select an intensity of light to be output by the one or more light sources 804 based at least in part on the detected intensity of the backscattered light. By way of example, if the detected intensity of the backscattered light decreases, the AGC unit may increase the intensity of the light output by the one or more light sources. Other examples of suitable intensity selection devices include, but are not limited to, dials, switches, buttons, keyboards, mice, touch screens, and other types of user interfaces known in the arts, which a user may use to select an intensity of light.

The base station has a setpoint temperature determination unit 886. As shown, the setpoint temperature determination unit may be electrically coupled with, or otherwise in communication with, the intensity selection device to receive the selected intensity. Alternatively, the setpoint temperature determination unit may determine the intensity of the light with a photodetector or otherwise. The setpoint temperature determination unit may determine a setpoint temperature 809 for the scanning fiber device based at least in part on the intensity of the light provided to the scanning fiber device through the interface.

The base station also includes the temperature controller 808. The temperature controller is electrically coupled with, or otherwise in communication with, the setpoint temperature determination unit. The temperature controller may receive, store, and use the determined setpoint temperature 809 for temperature control. The temperature controller is also electrically coupled with the interface. The temperature controller may provide one or more temperature control signals that are based, at least in part, on the determined setpoint temperature to the scanning fiber device through the interface. As shown, the temperature controller may also optionally be electrically coupled with the interface to receive sensed or measured conditions that may also be used for temperature control. In one or more embodiments of the invention, the temperature controller may include an algorithm, such as, for example, a proportional-integral-derivative (PID) algorithm, to determine the control signal based at least in part on the determined setpoint temperature and on the measured condition.

Figure 9:
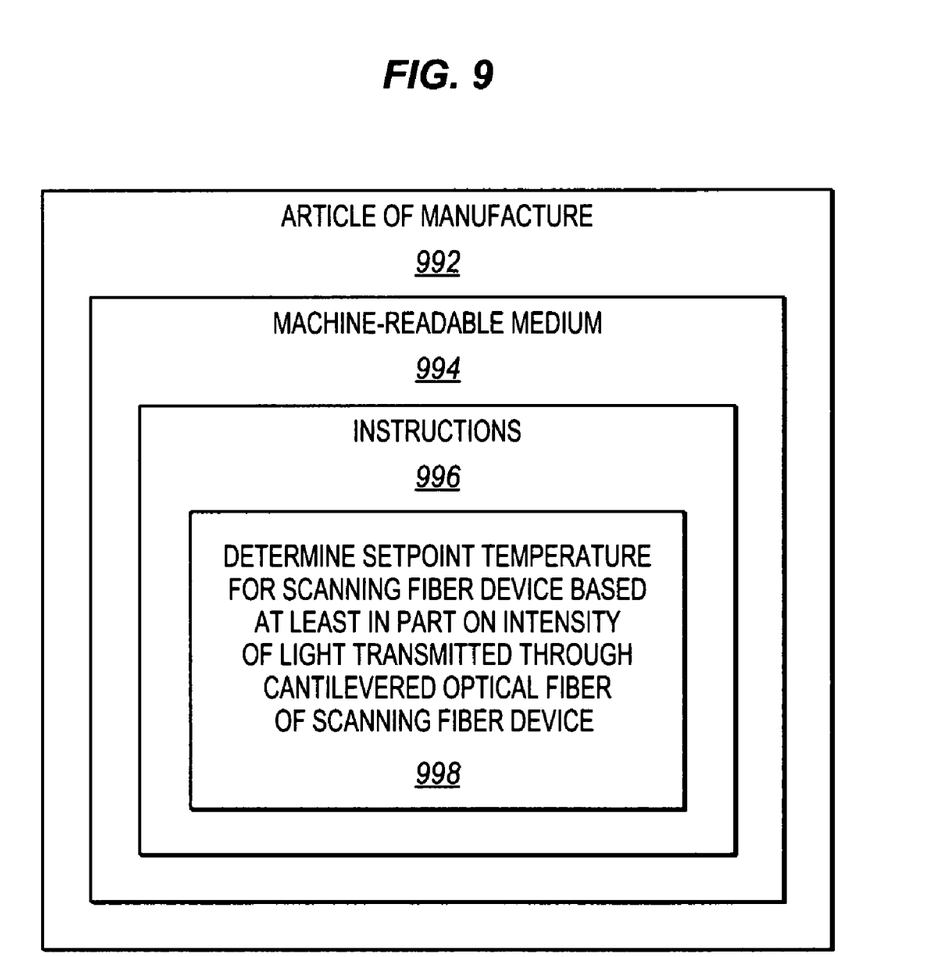
FIG. 9 is a block diagram of an article of manufacture including a machine-readable medium having stored thereon instructions to cause a machine to implement embodiments of the invention.

Each of the setpoint temperature determination unit and the temperature controller may be implemented in software (e.g., instructions stored on a machine-readable medium), firmware, hardware (e.g., a circuit), or a combination thereof. Furthermore, while the setpoint temperature determination unit and temperature controller are separated in the illustra- FIG. 9 is a block flow diagram of an article of manufacture 992, according to embodiments of the invention. The article of manufacture includes a machine-readable medium 994. Examples of suitable types of machine-readable mediums include, but are not limited to, optical storage mediums, optical disks, CD-ROMs, magnetic disks, magneto-optical disks, read only memories (ROMs), programmable ROMs (PROMs), erasable-and-programmable ROMs (EPROMs), electrically-erasable-and-programmable ROMs (EEPROMs), random access memories (RAMs), static-RAMs (SRAM), dynamic-RAMs (DRAMs), Flash memories, and combinations thereof.

The machine-readable medium is readable by a machine. Examples of suitable machines include, but are not limited to, base stations, endoscope base stations, scanning fiber systems, scanning fiber image acquisition systems, medical equipment, and computer systems, to name just a few examples.

Stored or otherwise provided in and/or on the machine-readable medium are instructions 996. The instructions include instructions 998 that if executed by the machine result in the machine determining a setpoint temperature for a scanning fiber device based, at least in part, on an intensity of light transmitted through a cantilevered optical fiber of the scanning fiber device. The instructions may include instructions to perform one or more other operations as described herein.

In the description above, for the purposes of explanation, numerous specific details have been set forth in order to provide a thorough understanding of the embodiments of the invention. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known circuits, structures, devices, and operations have been shown in block diagram form or without detail in order to avoid obscuring the understanding of the description. Where considered appropriate, terminal portions of reference numerals have been repeated among the figures to indicate corresponding or analogous elements, which may optionally have similar characteristics.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
    changing an intensity of light transmitted through a cantilevered optical fiber of a scanning fiber device; and
    changing a setpoint temperature for the scanning fiber device based at least in part on the change in the intensity of the light, wherein the change in the setpoint temperature is operable to substantially reduce a distortion in an image acquired with the scanning fiber device that would otherwise occur due at least in part to the change in the intensity.

2. The method of claim 1, wherein the change in the setpoint temperature is operable to substantially eliminate the distortion.

3. A method comprising:
    changing an intensity of light transmitted through a cantilevered optical fiber of a scanning fiber device;
    changing a setpoint temperature for the scanning fiber device based at least in part on the change in the intensity of the light; and
    acquiring an image using the scanning fiber device, and wherein acquiring the image comprises vibrating the cantilevered optical fiber within a Q-factor of a resonant frequency.

4. The method of claim 3, wherein the change in the setpoint temperature is operable to maintain a temperature of at least one of the cantilevered optical fiber and an adhesive attached to the cantilevered optical fiber substantially constant irrespective of the change in the intensity.

5. The method of claim 3, wherein changing the intensity comprises increasing the intensity, and wherein changing the setpoint temperature comprises decreasing the setpoint temperature.

6. The method of claim 3, wherein changing the intensity comprises decreasing the intensity, and wherein changing the setpoint temperature comprises increasing the setpoint temperature.

7. The method of claim 3, further comprising determining the change in the setpoint temperature based at least in part on a predetermined relationship between different setpoint temperatures and corresponding intensities of the light transmitted through the cantilevered optical fiber.

8. The method of claim 7, wherein determining the change in the setpoint temperature based at least in part on the predetermined relationship comprises determining the change in the setpoint temperature by evaluating at least one equation.

9. The method of claim 7, wherein determining the change in the setpoint temperature based at least in part on the predetermined relationship comprises determining the change in the setpoint temperature based at least in part on at least two pairs of data, each pair of data including a different intensity of light and a corresponding setpoint temperature.

10. The method of claim 3, wherein changing the setpoint temperature comprises gradually changing the setpoint temperature multiple times within a period of not more than several seconds after the intensity is changed.

11. A method comprising:
    changing an intensity of light transmitted through a cantilevered optical fiber of a scanning fiber device; and
    changing a setpoint temperature for the scanning fiber device based at least in part on the change in the intensity of the light,
    wherein the scanning fiber device comprises an endoscope, and wherein the method further comprises:
    inserting the endoscope into a patient; and
    acquiring an image of an inside of the patient.

12. An apparatus comprising:
an interface to couple with a scanning fiber device;
one or more light sources optically coupled with the interface to provide light to the scanning fiber device through the interface;
an actuator driver electrically coupled with the interface to provide actuator drive signals to the scanning fiber device through the interface;
a setpoint temperature determination unit to determine a setpoint temperature for the scanning fiber device based at least in part on an intensity of the light provided to the scanning fiber device through the interface, wherein the setpoint temperature determination unit is to determine a setpoint temperature that is operable to substantially reduce distortion in an image acquired with the scanning fiber device that would otherwise occur due at least in part to the intensity of the light; and
a temperature controller in communication with the setpoint temperature determination unit to receive the determined setpoint temperature, the temperature controller electrically coupled with the interface, the temperature controller to provide one or more temperature control signals that are based at least in part on the determined setpoint temperature to the scanning fiber device through the interface.

13. The apparatus of claim 12, wherein the setpoint temperature determination unit is to determine a setpoint temperature that is operable to substantially eliminate the distortion.

14. The apparatus of claim 12, further comprising the scanning fiber device coupled with the interface.

15. An apparatus comprising:
an interface to couple with a scanning fiber device;
one or more light sources optically coupled with the interface to provide light to the scanning fiber device through the interface;
an actuator driver electrically coupled with the interface to provide actuator drive signals to the scanning fiber device through the interface, wherein the actuator drive signals are operable to cause an actuator of the scanning fiber device to vibrate a cantilevered optical fiber of the scanning fiber device within a Q-factor of a resonant frequency;
a setpoint temperature determination unit to determine a setpoint temperature for the scanning fiber device based at least in part on an intensity of the light provided to the scanning fiber device through the interface; and
a temperature controller in communication with the setpoint temperature determination unit to receive the determined setpoint temperature the temperature controller electrically coupled with the interface, the temperature controller to provide one or more temperature control signals that are based at least in part on the determined setpoint temperature to the scanning fiber device through the interface.

16. The apparatus of claim 15, further comprising the scanning fiber device coupled with the interface.

17. An apparatus comprising:
an interface to couple with a scanning fiber device, wherein the scanning fiber device comprises a scanning fiber endoscope;
one or more light sources optically coupled with the interface to provide light to the scanning fiber device through the interface;
an actuator driver electrically coupled with the interface to provide actuator drive signals to the scanning fiber device through the interface;
a setpoint temperature determination unit to determine a setpoint temperature for the scanning fiber device based at least in part on an intensity of the light provided to the scanning fiber device through the interface; and
a temperature controller in communication with the setpoint temperature determination unit to receive the determined setpoint temperature, the temperature controller electrically coupled with the interface, the temperature controller to provide one or more temperature control signals that are based at least in part on the determined setpoint temperature to the scanning fiber device through the interface.

18. The apparatus of claim 17, wherein the setpoint temperature determination unit is to determine a setpoint temperature that is operable to maintain a temperature of at least one of a cantilevered optical fiber of the scanning fiber device and an adhesive coupled with the cantilevered optical fiber substantially constant irrespective of a change in the intensity.

19. The apparatus of claim 17, wherein the setpoint temperature determination unit is to determine a change in the setpoint temperature that is in an opposite direction to a change in the intensity.

20. The apparatus of claim 17, wherein the setpoint temperature determination unit is to determine the setpoint temperature based at least in part on a predetermined relationship between different intensities of light and corresponding setpoint temperatures.

21. The apparatus of claim 20, wherein the predetermined relationship comprises at least one equation relating the setpoint temperatures to the intensities.

22. The apparatus of claim 20, wherein the predetermined relationship comprises at least two pairs of data, each pair of data including a different intensity of light and a corresponding setpoint temperature.

23. The apparatus of claim 17, further comprising the scanning fiber device coupled with the interface.

24. An article of manufacture comprising:
a machine-readable medium having stored thereon instructions that when executed by a machine result in the machine performing operations including:
determining a setpoint temperature for a scanning fiber device based at least in part on an intensity of light transmitted through a cantilevered optical fiber of the scanning fiber device,
wherein the instructions that when executed by the machine result in the machine determining the setpoint temperature further include instructions that when executed by the machine result in the machine performing operations including:
determining a setpoint temperature that is operable to substantially reduce distortion in an image acquired with the scanning fiber device that would otherwise occur due at least in part to the intensity.

25. The article of manufacture of claim 24, wherein the instructions that when executed by the machine result in the machine determining the setpoint temperature further include instructions that when executed by the machine result in the machine performing operations including:
determining the setpoint temperature based at least in part on a predetermined relationship between intensities of light transmitted through the cantilevered optical fiber and corresponding setpoint temperatures.

26. The article of manufacture of claim 24, wherein the medium comprises one of a disk and a memory.

27. A method comprising:

transmitting a plurality of different intensities of light through a cantilevered optical fiber of a scanning fiber device; and for each of the different intensities, determining a setpoint temperature for the scanning fiber device that is operable to substantially reduce distortion in an image acquired with the scanning fiber device that would otherwise occur due at least in part to a respective one of the different intensities.

28. The method of claim 27, wherein determining the setpoint temperature comprises adjusting the setpoint temperature one or more times for each of the different intensities.

29. The method of claim 27, wherein determining a setpoint temperature for an intensity of the plurality comprises:

adjusting the setpoint temperature;

acquiring an image with the scanning fiber device while using the intensity and while controlling the scanning fiber device at the setpoint temperature; and examining the image for distortion.

30. The method of claim 29, further comprising:

determining whether the distortion is sufficiently reduced; and if the distortion is sufficiently reduced, then determining the setpoint temperature as the adjusted setpoint temperature; or if the distortion is not sufficiently reduced, then repeating said adjusting, said acquiring, and said determining.

31. The method of claim 27, wherein determining the setpoint temperature, for each of the different intensities, comprises determining a setpoint temperature that is operable to substantially eliminate the distortion.

32. The method of claim 27, further comprising generating an equation relating the different intensities to the respective determined setpoint temperatures.

* * * * *